(12) United States Patent
Lopez et al.

(10) Patent No.: US 7,019,655 B2
(45) Date of Patent: Mar. 28, 2006

(54) SYSTEM AND METHODS FOR DETECTING HARMFUL AGENTS WITHIN CONTENTS OF MAIL

(75) Inventors: Steven W. Lopez, Colorado Springs, CO (US); Jeffrey S. Whittle, Houston, TX (US)

(73) Assignee: Technology Solutions International, Inc., Colorado Springs, CO (US)

( * ) Notice: Subject to any disclaimer, the term of this patent is extended or adjusted under 35 U.S.C. 154(b) by 187 days.

(21) Appl. No.: 10/134,941

(22) Filed: Apr. 30, 2002

(65) Prior Publication Data

US 2003/0058099 A1 Mar. 27, 2003

Related U.S. Application Data

(63) Continuation of application No. 09/999,462, filed on Oct. 31, 2001.
(60) Provisional application No. 60/336,418, filed on Oct. 23, 2001.

(51) Int. Cl.
*G08B 17/00* (2006.01)

(52) U.S. Cl. .......................... 340/632; 73/23.2; 73/23.4
(58) Field of Classification Search ............. 340/573.1, 340/632; 73/23.2, 23.34; 222/52
See application file for complete search history.

(56) References Cited

U.S. PATENT DOCUMENTS

| | | | |
|---|---|---|---|
| 3,942,357 A | 3/1976 | Jenkins | |
| 5,078,952 A | 1/1992 | Gozani et al. | |
| 5,345,809 A | 9/1994 | Corrigan et al. | |
| 5,425,263 A | 6/1995 | Davies et al. | |
| 5,849,208 A | 12/1998 | Hayes et al. | |
| 5,855,652 A | 1/1999 | Talley | |

(Continued)

FOREIGN PATENT DOCUMENTS

| | | |
|---|---|---|
| EP | 0169057 | 1/1986 |
| EP | 1063602 | 12/2000 |
| JP | 10-288670 | * 10/1998 |
| WO | WO 02 29380 | 4/2002 |

OTHER PUBLICATIONS

U.S. News & World Report, "The Next Big Thing Is Small", by Phillip J. Longman; Janet Rae–Dupree; Charlie Petit, Jul. 3, 2000, pp. 1–5.

Earthfiles, "Blowing Up Dangerous Germs With Oily Nano Bombs", by Linda Moulton Howe, Copyright© 1999, pp. 1–5.

Nano Medicine, University of Michigan Education Department, Personnel, Resume for Dr. James R. Baker, Jr.

(Continued)

*Primary Examiner*—Julie Bichngoc Lieu
(74) *Attorney, Agent, or Firm*—Bracewell & Patterson

(57) ABSTRACT

A system and methods of the present invention advantageously provide efficient mail processing and handling that, as compared to existing procedures, enhances detection within the mail being processed or handled of biological, germ, chemical, or other harmful agents. A system and methods provide additionally a higher level of quality and consistency for processing and handling mail so that concerns over contamination of postal workers and potential mail recipients are reduced. A system and methods further provide enhanced disabling of contaminated mail contents, mail, mail equipment, mail containers, and mail personnel due to exposure or contact with harmful agents associated with mail. The system and methods preferably includes the use of at least one harmful agent sensor associated with mail processing equipment, and the at least one harmful agent sensor preferably includes at least one of the following: an olfactory device, an ultraviolet device, an infrared device, an x-ray device, a laser device, and a heat sensing device.

24 Claims, 9 Drawing Sheets-

U.S. PATENT DOCUMENTS

| | | | |
|---|---|---|---|
| 6,015,534 A | 1/2000 | Atwood | |
| 6,036,831 A | 3/2000 | Bishop | |
| 6,062,392 A | 5/2000 | Birmingham et al. | |
| 6,267,016 B1 | 7/2001 | Call et al. | |
| 6,290,065 B1 | 9/2001 | Kenning et al. | |
| 6,331,441 B1 | 12/2001 | Balch et al. | |
| 6,337,213 B1 | 1/2002 | Simon et al. | |
| 6,363,800 B1 | 4/2002 | Call et al. | |
| 6,532,275 B1 | 3/2003 | Haas | |
| 6,567,008 B1 | 5/2003 | Sansone | |
| 6,613,571 B1 | 9/2003 | Cordery et al. | |
| 6,684,682 B1 | 2/2004 | Stemmle et al. | |
| 6,695,146 B1 | 2/2004 | Call et al. | |
| 6,729,176 B1 | 5/2004 | Begin | |
| 6,740,836 B1 | 5/2004 | Ryan et al. | |
| 6,762,370 B1 | 7/2004 | Sansone | |
| 2002/0083022 A1 | 6/2002 | Algazi | |
| 2002/0124664 A1 | 9/2002 | Call et al. | |
| 2002/0126008 A1 | 9/2002 | Lopez et al. | |
| 2003/0058099 A1 | 3/2003 | Lopez et al. | |
| 2003/0085348 A1 * | 5/2003 | Megerle | 250/287 |
| 2004/0063197 A1 | 4/2004 | Tilles et al. | |
| 2004/0063198 A1 | 4/2004 | TIlles et al. | |

OTHER PUBLICATIONS

BioMailSolutions™ Detection System for Mail Processing, 2 pages, ww.lockheedmartin.com, www.LMDTech.com, © 2002 Lockheed Martin Corporation.

Unknown Author, "Scanna mail" Spring 2001, 5 pages.

Mail Performation Paddle Used During a Yellow Fever Epidemic, http://www.si.edu/postal/learnmore/paddle.html, Nov. 29, 2001.

"The Bugs of War," Nature, vol. 411, May 17, 2001.

Pinnick, R.G., et al., "Real–time Measurements of Fluorescence Spectra from Single Airborne Biological Particles," 1999.

SKC BioSampler brochure, 4 pages.

Hohnson–Winegar, A., et al., "The DoD Biological Detection Program, NDIA Roundtable Discussions," Oct. 24, 2000.

"Anthrax Detectors are Coming," Office of Naval Research, Oct. 29, 2001.

Ocean Optics Brochure, Endospore Detection, Dec. 5, 2001, www.oceanoptics.com.

Shanker, M.S., "Instant Anthrax Detector Developed in Hyderabad," Nov. 5, 2002.

Introduction to Fluorescense Techniques with Bibligraphy, Dec. 4, 2003, www.probes.com/handbook.

Cao, et al., DNA Nanoparticle Assembly and Diagnostics.

Ocean Optics Portable Endoscope Detection System Offers Real–time Anthrax Screening, Nov. 15, 2001.

Scholl, et al., "Immunoaffinity–based Phosphorescent Sensor Platform for the Detection of Bacterial Spores," abstract Apr. 2000

"What is Fluorometer!," Jul. 17, 2001, 1 pages, http://response.restoration.noaa.gov/oilaids/SMART/SMART-tour/fluor.html.

Hargis, et al., "Ultraviolet Fluorescence Identification of Protein, DNA and Bacteria," abstract, Feb. 1995.

McMillan, "Point–of–Care Real Time Molecular Detection of Infectious Agents," May 20, 2001.

"Cellomics, Inc. Announces the Development of Biowarfare Detection Methods," Nov. 21, 2001, 222.prnewswire.com.

"Lambda Technologies' Variable Microwave Systems Adapted to 'Zap' Bioterrorism Threat," Nov. 5, 2001, www.prnewswire.com.

"Egea Awarded Second DARPA Contract to Fight Bioterrorism," Oct. 30, 2001.

Meserve, J., "Feds, industry rush to make cheap biohazard detectors," Nov. 1, 200.

"Mathematical model provides new tool to assess mail–bourne spread of anthrax," May 13, 2002.

"UMAss chemist working on sensors that could eventually identify bioterror agents," Dec. 13, 2001.

"Stickers warn of UV Radiation," Mary 23, 2000.

"Simple and inexpensive, an artificial nose senses smell by seeing colors," Aug. 16, 2000.

"Electronic Sniffer, Listen Hard and Listen Good if You Want to Name That Smell," Dec. 19, 2000, www.newscientist.com.

E–Noses Out Mines, Office of Naval Research, Apr. 17, 2001.

"On a Spot Smaller Than A Dime, UB Chemists Print Sensors that May Detect Hundreds of Chemicals," Jan. 25, 2002.

"The Classica Group Files Patent Application for its Method of Sterilzation Against Anthra Bateria Diseminated on or in Paper" Oct. 26, 2001, businesswire.

Gordon, M., "Companies Accused of Anthrax Fraud," Nov. 15, 2001.

"Sensors Detect Biological Weapons," www.photonics.com/content/jan99/techweapons.html Jan. 1994.

Aston, C., "Biological Warfare Canaries," IEEE Spectrum, Oct. 2001.

Murray, C., Biodetectors aim to broaden search for anthrax bacteria, Oct. 15, 2001.

"Biosensors and Biochips for Environmental and Biomedical Applications," www.ornl.gov/virtual/biosensor Dec. 4, 2001.

"ID Mail Systems to Develop Mail Profiling System for In–Bound Mail Centers Against Potential Threatening Mail," Oct. 18, 2001.

"Mailrooms on Front Lines in Bioterrorism Fight," Oct. 15, 2001, The Wall Street Journal.

Vorenberg, S., "Sandia designs sensors to detect toxic chemicals in water," Oct. 12, 2001, www.abqtrib.com.

"Sandia's soil and groundwater chemical 'sniffer' may help protect the nations' water supply," Oct. 3, 2001, www.sandia.gov/media/newsrel.nr2001/whtsniff.htm.

"Two New Sandia 'sniffers' expand law enforcement abilities to detect explosives and narcotics," Nov. 30, 1999, www.sandia.gov/media/newsrel.nr1999/sniffers.htm.

U.S. News & World Report, "The Next Big Thing Is Small", by Phillip J. Longman; Janet Rae–Dupree; Charlie Petit, Jul. 3, 2000, pp. 1–5.

Earthfiles, "Blowing Up Dangerous Germs With Oily Nano Bombs", by Linda Moulton Howe, Copyright © 1999, pp. 1–5.

Nano Medicine, University of Michigan Education Department, Personnel, Resume for Dr. James R. Baker, Jr.

BioMailSolutions™ Detection System for Mail Processing, 2 pages, www.lockheedmartin.com, www.LMDTech.com, © 2002 Lockheed Martin Corporation.

Unknown Author, "Scanna mail" Spring 2001, 5 pages.

Mail Performation Paddle Used During a Yellow Fever Epidemic, http://www.si.edu/postal/learnmore/paddle.html, Nov. 29, 2001.

"The Bugs of War," vol. 411, May 17, 2001.
Pinnick, R.G., et al., "Real–time Measurements of Fluorescence Spectra from Single Airborne Biological Particles," 1999.
SKC BioSampler brochure, 4 pages.
Hohnson–Winegar, A., et al., "The DoD Biological Detection Program, NDIA Roundtable Discussions," Oct. 24, 2000.
"Anthrax Detectors are Coming," Office of Naval Research, Oct. 29, 2001.
Ocean Optics Brochure, Endospore Detection, Dec. 5, 2001, www.oceanoptics.com.
Shanker, M.S., "Instant Anthrax Detector Developed in Hyderabad," Nov. 5, 2002.
Introduction to Fluorescense Techniques with Bibligraphy, Dec. 4, 2003, www.probes.com/handbook.
Cao, et al., DNA Nanoparticles Assembly and Diagnostics.
Ocean Optics Portable Endoscope Detection System Offers Real–time Anthrax Screening, Nov. 15, 2001.
Scholl, et al., "Immunoaffinity–based Phosphorescent Sensor Platform for the Detection of Bacterial Spores," abstract Apr. 2000.
"What is Fluorometer?," Jul. 17, 2001, 1 page, http://response.restoration.noaa.gov/oilaids/SMART/SMART-tour/fluor.html.
Hargis, et al., "Ultraviolet Fluorescence Identification of Protein, DNA and Bacteria," abstract, Feb. 1995.
McMillan, "Point–of–Care Real Time Molecular Detection of Infectious Agents," May 20, 2001.
"Cellomics, Inc. Announces the Development of Biowarfare Detection Methods," Nov. 21, 2001, www.prnewswire.com.
"Lambda Technologies' Variable Microwave Systems Adapted to 'Zap' Bioterrorism Threat," Nov. 5, 2001, www.prnewswire.com.
"Egea Awarded Second DARPA Contract to Fight Bioterrorism," Oct. 30, 2001.
Meserve, J., "Feds, industry rush to make cheap biohazard detectors," Nov. 1, 200'.
"Mathematical model provides new tool to assess mail–bourne spread of anthrax," May 13, 2002.
"UMAss chemist working on sensors that could eventually identify bioterror agents," Dec. 13, 2001.

"Stickers warn of UV Radiation," Mary 23, 2000.
"Simple and inexpensive, an artificial nose senses smell by seeing colors," Aug. 16, 2000.
"Electronic Sniffer, Listen Hard and Listen Good if You Want to Name That Smell," Dec. 19, 2000, www.newscientist.com.
E–Noses Out Mines, Office of Naval Research, Apr. 17, 2001.
"On a Spot Smaller Than A Dime, UB Chemists Print Sensors that May Detect Hundreds of Chemicals," Jan. 25, 2002.
"The Classica Group Files Patent Application for its Method of Sterilzation Against Anthra Bateria Disseminated on or in Paper" Oct. 26, 2001, businesswire.
Gordon, M., "Companies Accused of Anthrax Fraud," Nov. 15, 2001.
"Sensors Detect Biological Weapons," www.photonics.com/content/jan99/techweapons.html Jan. 1994.
Aston, C., "Biological Warfare Canaries," IEEE Spectrum, Oct. 2001.
Murray, C., Biodetectors aim to broaden search for anthrax bacteria, Oct. 15, 2001.
"Biosensors and Biochips for Environmental and Biomedical Applications," www.ornl.gov/virtual/biosensor Dec. 4, 2001.
"ID Mail Systems to Develop Mail Profiling System for In–Bound Mail Centers Against Potential Threatening Mail," Oct 18, 2001.
"Mailrooms on Front Lines in Bioterrorism Fight," Oct. 15, 2001, The Wall Street Journal.
Vorenberg, S., "Sandia designs sensors to detect toxic chemicals in water," Oct. 12, 2001, www.abqtrib.com.
"Sandia's soil and ground water chemical 'sniffer' may help protect the nations' water supply," Oct. 3, 2001. www.sandia.gov/media/newsrel.nr2001/whtsniff.htm.
"Two New Sandia 'sniffers' expand law enforcement abilities to detect explosives and narcotics," Nov 30, 1999, www.sandia.gov/media/newsrel.nr1999/sniffers.htm.

* cited by examiner

SYSTEM AND METHODS FOR DETECTING HARMFUL AGENTS WITHIN CONTENTS OF MAIL

RELATED APPLICATIONS

This application is a continuation of U.S. Non-Provisional Patent Application Serial No. 09/999,462 titled "System and Method For Detecting Harmful Agents Within Contents of Mails" filed on Oct. 31, 2001 and claims the benefits of U.S. Provisional Patent Application Serial No. 60/336,418 filed on Oct. 23, 2001, both are incorporated herein by reference in its entirety.

FIELD OF THE INVENTION

The present invention relates to the field of postal handling, processing, and delivery and, more particularly, to detecting contents of letters, flats, packages, or other mail.

BACKGROUND OF THE INVENTION

Even though threats and other actions by terrorist and fringe groups have occurred with biological, germ, chemical, or other harmful agents over the years, more recent developments have brought such threats to the forefront of the public thought and action. Postal and delivery firms, however, continue to face significant problems with biological, germ, chemical, and other harmful agents that are likely to cause injury, sickness, or death when handled by the transportation or delivery firm or when opened by the intended recipient of a mailpiece or package. The U.S. Postal Service (USPS) has declared that safety of all people processing, delivering and receiving mail must be given the highest priority.

The complexity of detection of contents of a letter, flat, or package within the USPS or other mail or parcel delivery service is immense. The USPS, for example, handles over 680 million pieces of mail every day collected from as many as 100 million points (assuming residential and businesses may leave mail for the delivery carrier to pick up). In the U.S. alone, there are up to 500 processing centers collecting mail from over 28,000 post offices which, in turn, collect mail from mail drops or collection boxes that easily number over one million. It can be practically impossible to have personalized inspectors located at each mail drop or collection box. For example, the cost can be prohibitive, the environments are not well controlled, and mail drop or other mail boxes can be subject to bypass by handling mail directly to a delivery carrier.

Also, in the USPS, there are three primary types of mail categories. For example, letters and postcards are, by USPS definition, no larger than 6.125 inches by 11.5 inches or ¼ inch thick. Flats are larger than letters but no larger than 12 inches by 15 inches or 1.25 inches thick. Parcels are any mailpiece that exceeds a flat dimension. Letters are typically processed by different equipment than flats or parcels due to the difference in the physical characteristics. Accordingly, because of the different sizes, shapes, and weight of mail and the different processing stations within postal service companies, detecting biological, germ, chemical, and other harmful agents within the mail can be even more difficult. Further, to add to the complexity, as described above, mail and mail packaging also can be composed of different materials other than just paper or organic products which, in turn, makes it even more difficult to process and handle.

SUMMARY OF THE INVENTION

With the foregoing in mind, the system and methods of the present invention advantageously provide efficient mail processing and handling that, as compared to existing procedures, enhances detection within the mail being processed or handled of biological, germ, chemical, or other harmful agents. The system and methods provide additionally a higher level of quality and consistency for processing and handling mail so that concerns over contamination of postal workers and potential mail recipients are reduced.

The present invention advantageously provides a system, product, and methods to disable or decontaminate mail having harmful agents associated therewith. The present invention also advantageously provides a system which examines mailpieces at the earliest point in the collection and distribution process for each type of mail. Therefore, the system preferably detects the presence of harmful agents prior to handling or opening. Alternatively, to enhance protection of postal carriers, the present invention also can provide a type of biological, germ, chemical, or other harmful agent detection sensor at each mail drop or collection box by providing drivers or vehicles with preliminary detection capabilities to enhance protection of a driver.

More particularly, the present invention provides a system for detecting harmful agents within the contents of mail which preferably includes at least one piece of mail processing equipment positioned within a mail processing facility, at least one harmful agent sensors positioned adjacent the at least one piece of mail processing equipment to sense the presence of a harmful agent in each individual piece of mail as the mail is processed by each of the plurality of pieces of mail processing equipment, at least one system processor in communication with the at least one harmful agent sensors to process data received therefrom, and at least one alarm indicator responsive to the at least one system processor to indicate that the at least one harmful agent sensor has sensed the presence of a harmful agent.

According to other aspects of the present invention a system for detecting harmful agents within the contents of mail is provided which preferably includes a plurality of pieces of mail processing equipment positioned within a mail processing facility, a plurality of harmful agent sensors each positioned adjacent one of the plurality of pieces of mail processing equipment to sense the presence of a harmful agent in each individual piece of mail as the mail is processed by each of the plurality of pieces of mail processing equipment, at least one system processor in communication with each of the plurality of harmful agent sensors to process data received from the plurality of harmful agent sensors, and at least one alarm indicator responsive to the at least one system processor to indicate that at least one of the plurality of harmful agent sensors has sensed the presence of a harmful agent.

Due to the difference in handling processes, the location of detection equipment preferably is based on the requirements of the processing equipment currently utilized. A system according to the present invention preferably uses methods of detection by physically touching, smelling, or sensing each mailpiece after the mailpiece has been introduced into processing equipment and separated from each other. This sensing preferably is performed at high speed, typically more than 15 pieces per second, using a variety of methods for agent detection. For example, laser scanning or pulsing detection systems, sensor "sniffers" that are as small as a microchip and can process instantly, and ultraviolet light can also be used in order to retard the growth of bacteria. In addition, other methods can be used as well as understood by those skilled in the art as the threat of anthrax, smallpox, and other biological warfare agents are currently prevalent.

Olfactory systems or machines which smell or sense different agents can be used as well. These olfactory systems also can be mounted to vehicles or carried by deliverers as a preliminary detection system for mail carriers, e.g., using hand-held sensors or machines mounted to the vehicle such as provided with olfactory machines or other types of sensors. The hand-held sensor has the benefit of providing the carrier early detection prior to removing bulk mail from a mail box, drop box, or other collection box or location.

The present invention also advantageously includes methods of detecting and methods of disabling harmful agents associated with pieces of mail. A method of detecting the presence of a harmful agent associated with mail preferably includes smell sensing the presence of one of a plurality of harmful agents possibly associated with the contents of mail by the use of an olfactory device and indicating an alarm condition responsive to the sensed presence of one of a plurality of harmful agents.

For detection within a mail handling facility, a system for letters according to the present invention is to require that all non-verified and all unique mailpieces be processed through a piece of equipment that will cancel and face mailpieces. This process requires that the mailpieces be individually separated and then individually canceled with a mechanical ink impression. This process allows for the sensors to act individually on each mailpiece to thereby increase the accuracy and ensure proper identification of the offending mailpiece.

For flats, the system is similar to that of letters except the equipment is typically called a Model 15 flats canceler. This equipment also separates and mechanically cancels that mailpiece, although at a substantially slower speed than letters. Since the canceler physically touches the envelope and causes the contents to be "shifted and shaken-up"0 it would allow certain biological, germ, chemical or other harmful agent sensors to examine each mailpiece as the mailpiece passes by the device therefore detecting these harmful agents inside.

For parcels, the system ensures separation is performed by mechanical equipment prior to directing the sensing devices towards the parcel. The equipment used for processing parcels is more varied but requires that the mailpiece be separated prior to the sortation process.

An embodiment of the present invention also includes a system for detecting harmful agents within the contents of mail having at least one piece of mail processing equipment adapted to be positioned within a mail processing facility to individually separate and contactingly capture each of a plurality of pieces of mail between a plurality of belts as the plurality of pieces of mail pass through the at least one piece of mail processing equipment at a relatively high rate of speed, at least one harmful agent sensor adapted to be positioned adjacent the at least one piece of mail processing equipment to sense the presence of a harmful agent in each individual piece of mail as the mail is processed by the at least one piece of mail processing equipment, at least one system processor in communication with the at least one harmful agent sensor to process data received therefrom, and at least one alarm indicator responsive to the at least one system processor to indicate that the at least one harmful agent sensor has sensed the presence of a harmful agent.

An embodiment of the present invention additionally provides a method of detecting the presence of a harmful agent associated with mail including contactingly capturing each of a plurality of separate pieces of mail between a plurality of belts as the plurality of separate pieces of mail travel at a relatively high rate of speed, sensing the presence of one of a plurality of harmful agents possibly associated with the contents of mail by the use of a harmful agent sensor after the mail has been contactingly captured between a plurality of belts, and indicating an alarm condition responsive to the sensed presence of one of a plurality of harmful agents.

Still further, a system of detecting and disabling harmful agents in mail is also provided which applies a "nanobomb" or other disabling agent in mail processing ink or other mail associated fluid such as associated with a mail canceling station, a bar code application station, or other station where ink or other mail processing fluid is often applied, or any other application of mail processing ink as understood by those skilled in the art. For example, within an ink pad, ink material itself, or other fluid location a disabling biological or chemical agent or reactant can be located so that when individual pieces of mail are stamped as being canceled or processed, the postal workers handling mail have increased confidence that mail passing through the station is disabled or decontaminated. This can also be accomplished when a bar-code or a visible identification tag marker or other indicia which has ink or other printed material is applied to an article of mail. So, in essence, detection or mass processing is provided by the disabling agent itself within the ink or other locations to which the ink is associated, e.g., applied to material of the pad itself of an ink pad.

A system for disabling harmful agents in contents of or associated with mail is also provided according to further aspects of the present invention. The system preferably includes at least one piece of mail processing equipment positioned to process a plurality of pieces of mail and a harmful agent disabling fluid applicator associated with the at least one piece of mail processing equipment and positioned to apply a harmful agent disabling fluid to a plurality of pieces of mail being processed to thereby disable harmful agents within the plurality of pieces of mail during one of the following conditions: when all of the plurality of mail pieces pass through at least one of the plurality of pieces of mail processing equipment, when the presence of a harmful agent is detected in a mail piece being processed, or when the absence of a harmful agent is detected in a mail piece being processed.

The present invention also includes a method of disabling a harmful agent associated with a piece of mail. The method preferably includes applying a harmful agent disabling fluid, e.g., liquid, gas, mist, or spray, associated with processing mail to one or more mail pieces, e.g., to each of or a bundle, group, set, or container of a plurality of mail pieces.

Accordingly, a system and methods of detecting harmful agents within contents of mail of the present invention advantageously provides a lower cost, more effective, and enhanced redundancy solution to substantially reduce the likelihood of passing on mail having harmful agents to postal customers. The mail processing system and methods also advantageously reduces risk of exposure to carriers and handlers of mail by early and redundant detection.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION

Figure 1:
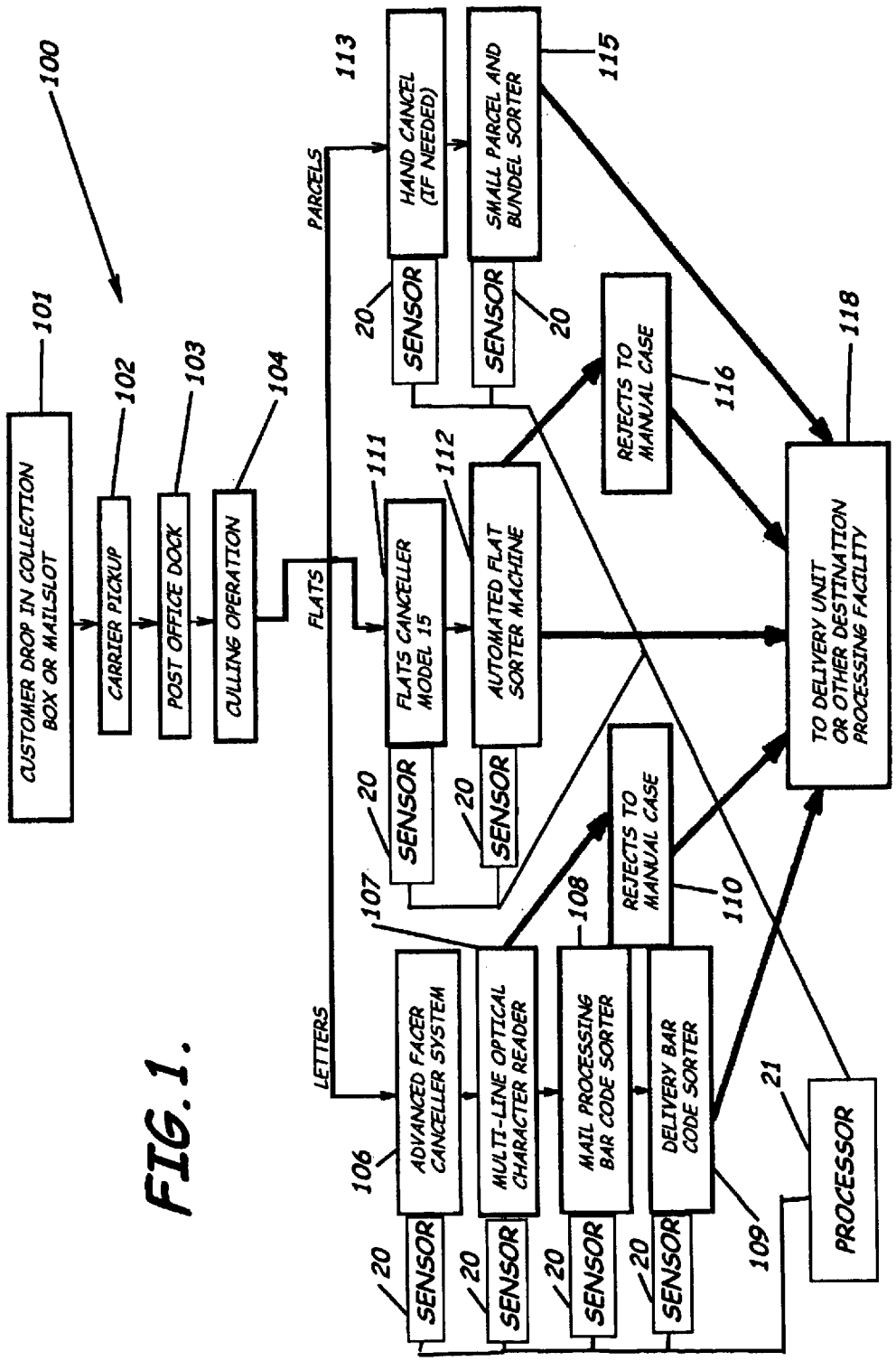
FIG. 1 is a schematic block diagram of a process flow for detecting and handling mail for a system for detecting harmful agents in contents of mail according to a first embodiment of the present invention.

The present invention will now be described more fully hereinafter with reference to the accompanying drawings which illustrate preferred embodiments of the invention. This invention, however, may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. The prime notation, if used, indicates similar elements in alternative embodiments.

As illustrated in FIGS. 1-9, the highest level of reduced risk from contamination or exposure due to harmful agents in contents of mail M, for example, preferably is achieved by using multiple levels of detection, e.g., multiple sensors 20 or multiple types of sensors within a system 15. The first level, for example, preferably is to allow animals (e.g., dogs) or olfactory systems as understood by those skill in the art to smell or sniff mail that is typically found in bulk containers waiting for processing or in the process of being transferred (dumped) for processing (see FIGS. 3-4). Although animals have been trained to detect agents by smell, it may be impractical to detect biological, germ, chemical or other harmful agents within individual pieces of mail with manual methods (human or animal), due to the large numbers of individual mailpieces being processed on a daily basis, e.g., over 680 million pieces of mail every day collected from as many as 100 million points (assuming residential and businesses may leave mail for the delivery carrier to pick up).

A system 15 according to the present invention preferably uses a preferred method of detection by physically touching, smelling, or sensing each mailpiece M after it has been introduced into processing equipment, e.g., 50, 60, 70, 80, and separated from each other. This sensing preferably is performed at high speed, typically more, than 15 pieces per second, using one or more of a variety of methods for agent detection. For example, laser scanning or pulsing detection systems, sensor "sniffers" that are as small as a microchip and can process instantly, and ultraviolet light can also be used in order to retard the growth of bacteria as understood by those skilled in the art. In addition, other methods can be used as well as understood by those skilled in the art as the threat of anthrax, smallpox, and other biological warfare agents are currently prevalent. Olfactory systems or machines 30 which smell or sense different agents can be used as well. These olfactory systems 30 also can be mounted to vehicles T as a preliminary detection system 30' for mail carriers, e.g., using hand-held sensors 30" or machines 30' mounted to the vehicle (see FIGS. 4-5). The hand-held sensor 30" has the benefit of providing the carrier early detection prior to removing bulk mail from a mail box, drop box, or other collection box or location.

A system 15 for detecting harmful agents within contents of or associated with mail is provided as illustrated. The system 15 preferably has a plurality of pieces of mail processing equipment 60, 70, 80 positioned within a mail processing facility (see FIG. 4) and a plurality of harmful agent sensors 20 each positioned adjacent one, e.g., mounted to, connected to, or positioned with a housing of, the plurality of pieces of mail processing equipment 60, 70, 80 to sense the presence of a harmful agent in each individual piece of mail M as the mail is processed by each of the plurality of pieces of mail processing equipment 60, 70, 80. At least one system processor 31, such as provided by a computer, a microprocessor, or software and/or hardware device, is positioned in communication with each of the plurality of harmful agent sensors 20 to process data received from the plurality of harmful agent sensors 20. At least one alarm indicator 33, such as a bell, a light, a signal, or other indication, is responsive to the at least one system processor 31 to indicate that at least one of the plurality of harmful agent sensors 20 has sensed the presence of a harmful agent. Advantageously, an automated dialer or other notification device 35 can be connected to or positioned in communication with the processor 31 and/or alarm 33 to dial for emergency help if desired should a harmful agent be detected.

Figure 2:
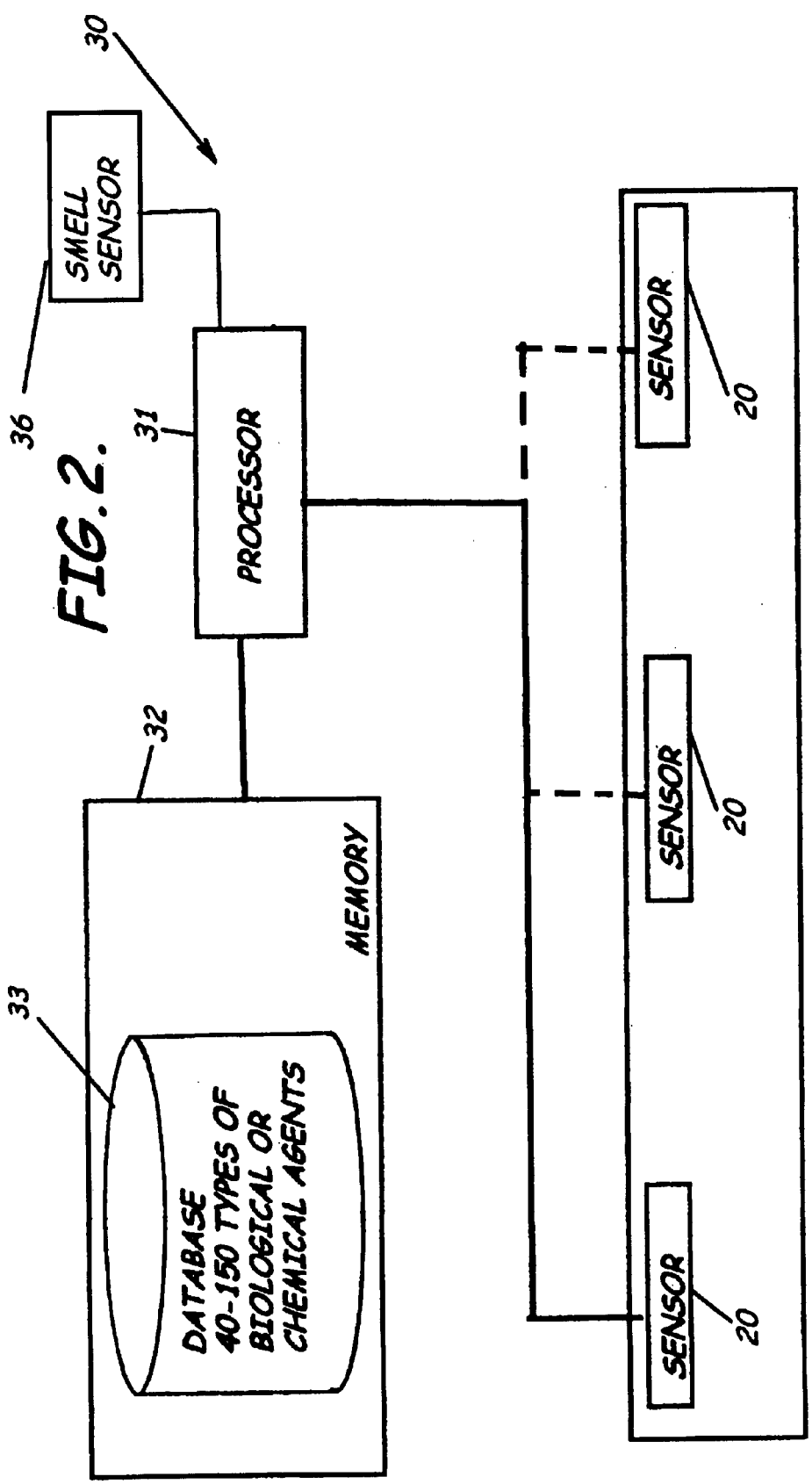
FIG. 2 is a schematic block diagram of a system for detecting harmful agents in contents of mail according to a first embodiment of the present invention.
Figure 3:
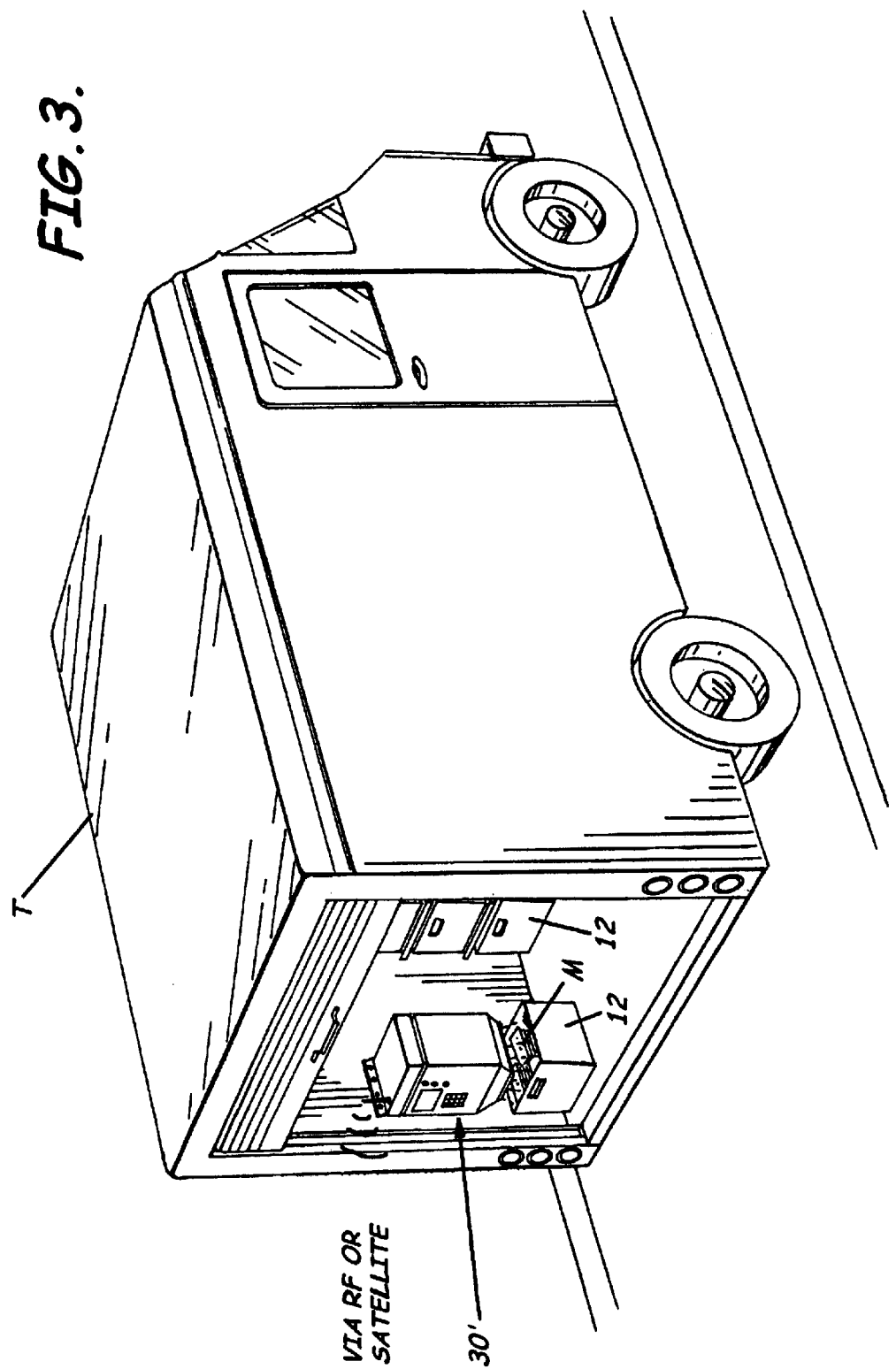
FIG. 3 is an environmental perspective view of a system for detecting harmful agents in contents of mail according to a first embodiment of the present invention.

At least one of the plurality of harmful agent sensors 20 preferably is provided by an olfactory device 30 which includes a smell sensor positioned to sense smell associated with a piece of mail, an olfactory device processor 31 in communication with the smell sensor to process data received from the smell sensor, and a memory 32 in communication with the olfactory device processor 31 to store smell sensing data to be processed by the olfactory device processor (see FIG. 2). Alternatively to or in addition to the above, the at least one of the plurality of harmful agent sensors 20 can be provided by at least one of the following: an olfactory device 30, an ultraviolet device, an infrared device, an x-ray device, a laser device, a radio frequency device, and a heat sensing device.

The system 15 can also include a harmful agent disabling fluid applicator 40 positioned to apply a harmful agent disabling fluid 45 to a plurality of pieces of mail M being processed to thereby disable harmful agents within the plurality of pieces of mail M during one of the following conditions: when all of the plurality of mail pieces M pass through at least one of the plurality of pieces of mail processing equipment 50, 60, 70, 80, 90, when the presence of a harmful agent is detected in a mail piece M being processed, or when the absence of a harmful agent is detected in a mail piece M being processed. The harmful agent disabling fluid applicator 40 preferably includes a fluid storage container 42 positioned to supply the harmful agent disabling fluid 45 for application to each of the plurality of pieces of mail M such as through a supply line or tube 43. The harmful agent disabling fluid 45 preferably is provided by either a liquid, a gas, or a combination thereof. As described further herein, the harmful agent disabling fluid 45 preferably includes a nanobomb material 47 such as a nanoemulsion or other nanobomb material as understood by those skilled in the art. For example, the harmful agent disabling fluid can advantageously include an ink 45 having the nanobomb material 47 associated therewith, such as premixed or supplied from an additive container 44 having the nanobomb material positioned therein and supplied to the fluid container 42 through another supply line 46. This allows the ink 45 to be used in conjunction with the mail M in various applications without substantial risk to those contacting the mail M and with little or no indication of its presence on the mail.

The nanobomb material 47, for example, is preferably a plurality of uniformly sized droplets in a size range of about 200 nanometers to about 400 nanometers and is preferably an antimicrobial solution. Although this size and type currently have particular advantages, the term nanobomb is used herein, however, can be liquids, gases, or combinations thereof having smaller or slightly larger particle sizes as well as understood by those skilled in the art. Advantageously, for example, the harmful agent disabling fluid further includes an ink having the nanobomb material associated therewith, and the ink is applied to each of the plurality of mail pieces M being processed (see FIG. 6).

Also, for example, an olfactory machine or sensor 30, 30', 30", as understood by those skilled in the art, of a system 15 according to the present invention preferably has data stored in memory 32 indicative of, representative of, or related to a plurality of biological, germ, chemical, or other harmful agents which have previously been isolated by the study of olfactory systems using humans or animals. These machines can then advantageously have a look-up table or a database stored in memory 32 and a processor 31 in communication with the memory 32 and one or more of a plurality of sensors 20 for processing and comparing sensed smells with this data in the look-up table to determine whether the sensed smell is a potential harmful agent. If so, then such mail M can be sent to an isolation station, alarms sounded or transmitted, and the mail M further inspected by protected investigators to determine its contents and source. The look up table or database of the memory 32 preferably has a plurality, e.g., about 40 to about 150, different potential harmful agents commonly associated with biological, germ, or chemical warfare such as described herein, e.g., small pox, Anthrax, HIV, Herpes, Hepatitis and various other bacteria, viruses, disease causing or other chemical agents. These systems 15 can then advantageously be added to or updated as new potentially harmful agents are developed, and the database advantageously be kept confidential so that only qualified inspectors or investigators know the list of agents. The database can then be updated remotely, e.g., by a communications network such as the Internet or a local area network, satellite, or radio frequency, infrared, or on-site to various locations throughout the country. Remote updating to confidential databases, e.g., with encrypted code, advantageously allows postal delivery companies to maintain low cost communication with the postal carriers and handlers throughout a postal delivery network and at postal handling and processing locations.

For detection within a mail handling facility, for example, a method of detection for letters according to the present invention is to require that all non-verified and all unique mailpieces M be processed through a piece of equipment that will cancel and face mailpieces M such as with an advance facer canceler system 106 as understood by those skilled in the art. This process requires that the mailpieces M be individually separated and then individually canceled with a mechanical ink impression. This process allows for the sensors 20 to act individually on each mailpiece M, thereby increasing the accuracy and ensuring proper identification of the offending mailpiece M. Additionally, such processes allow nanobombs, as understood by those skilled in the art, to be formed in ink, a spray mist, or other fluids, e.g., liquids or gas, associated with mail processing such that when the ink, spray mist, gas or other fluid is applied to the mail M, the ink or fluid disables the harmful agents within the mail M.

As understood by those skilled in the art, nanobombs, for example, are preferably small antimicrobial, i.e., kill or disable microbes, or antichemical, i.e., disables, dilutes, or changes chemicals, agents that employ uniformly sized droplets in the 200–400 nanometer range. For example, nanobio antimicrobial nanoemulsions are water/oil emulsions that employ uniformly sized droplets in the 200–400 nanometer range. These droplets can be stabilized by surfactant and can be responsible for cidal or cidal agent activity. In concentrated form, the nanoemulsions can be formulated in a variety of carriers allowing for gels, creams, sprays, mists, liquid and gas products to be used in conjunction with the emulsion. These nanobombs preferably have no toxicity.

The nanobomb preferably destroys microbes effectively without toxicity or harmful residual effects and eradicates, destroys, or disables viruses such as HIV and Herpes, bacteria such as *E. coli* and *Salmonella*, spores such as Anthrax, fungi such as *Candida albicans, Byssochlamys fulva*, disease causing agents such as Smallpox, and other harmful agents as understood by those skilled in the art. Also, nanoemulsions can be formulated to kill only one or two selected classes of microbes as desired. The nanobomb is preferably a non-toxic, non-corrosive, bio-defense decon material that can decontaminate equipment, personnel, structures, terrain, and, more particularly, mail, mail equipment, mail containers, and mail handling personnel in the event of a bioincident or other harmful agent being present in, present on, or associated with mail, equipment, containers or personnel. Examples of this nanobomb technology or products can be seen and made available by companies such as NanoBio Corporation of Ann Arbor, Mich. Liquid or gas products can be used to decontaminate trays or boxes of mail as well by spray, mist, immersion, or other exposure techniques as understood by those skilled in the art.

Figure 4:
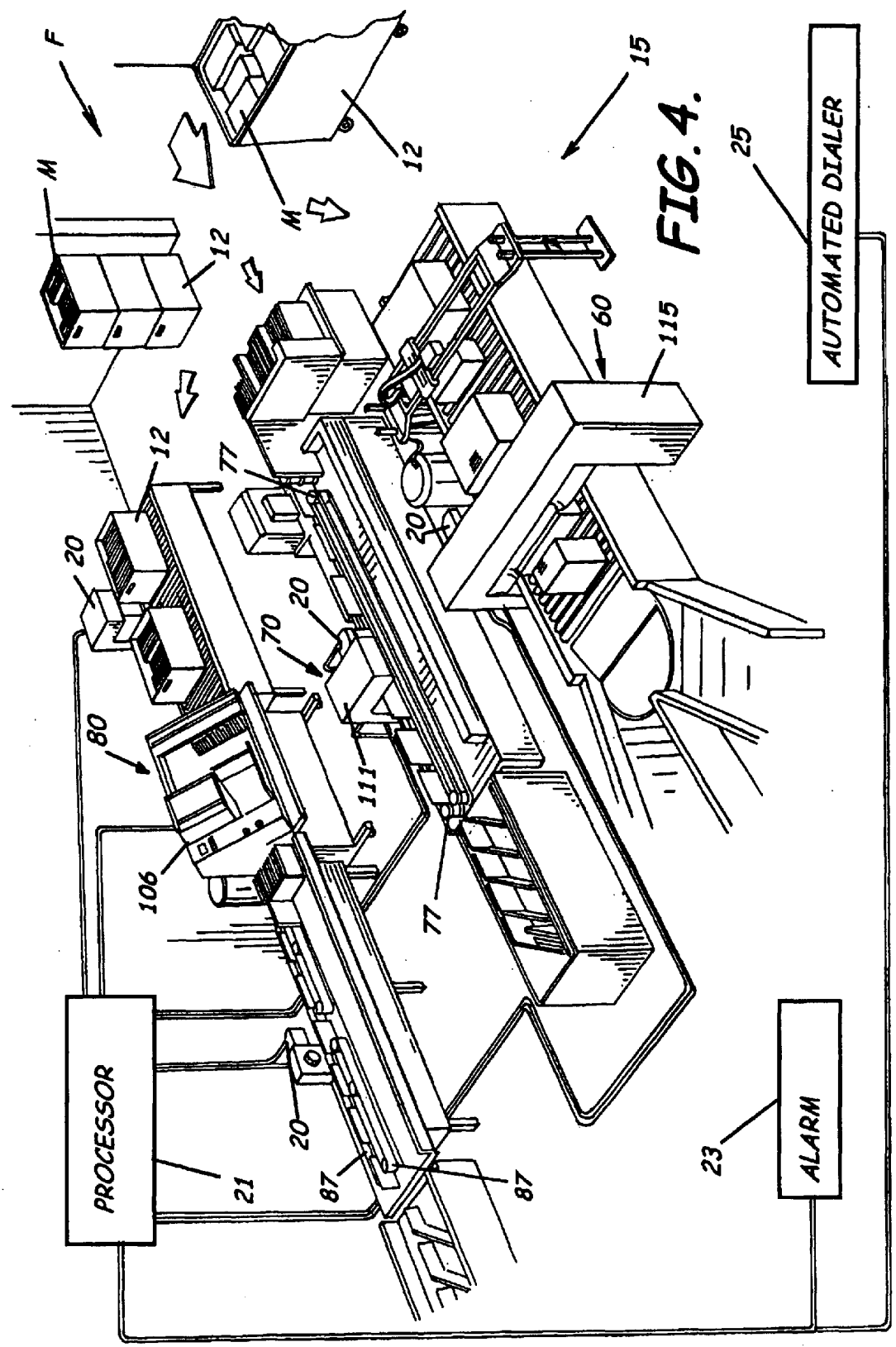
FIG. 4 is an environmental perspective view of a system for detecting harmful agents in contents of mail according to a first embodiment of the present invention.
Figure 5:
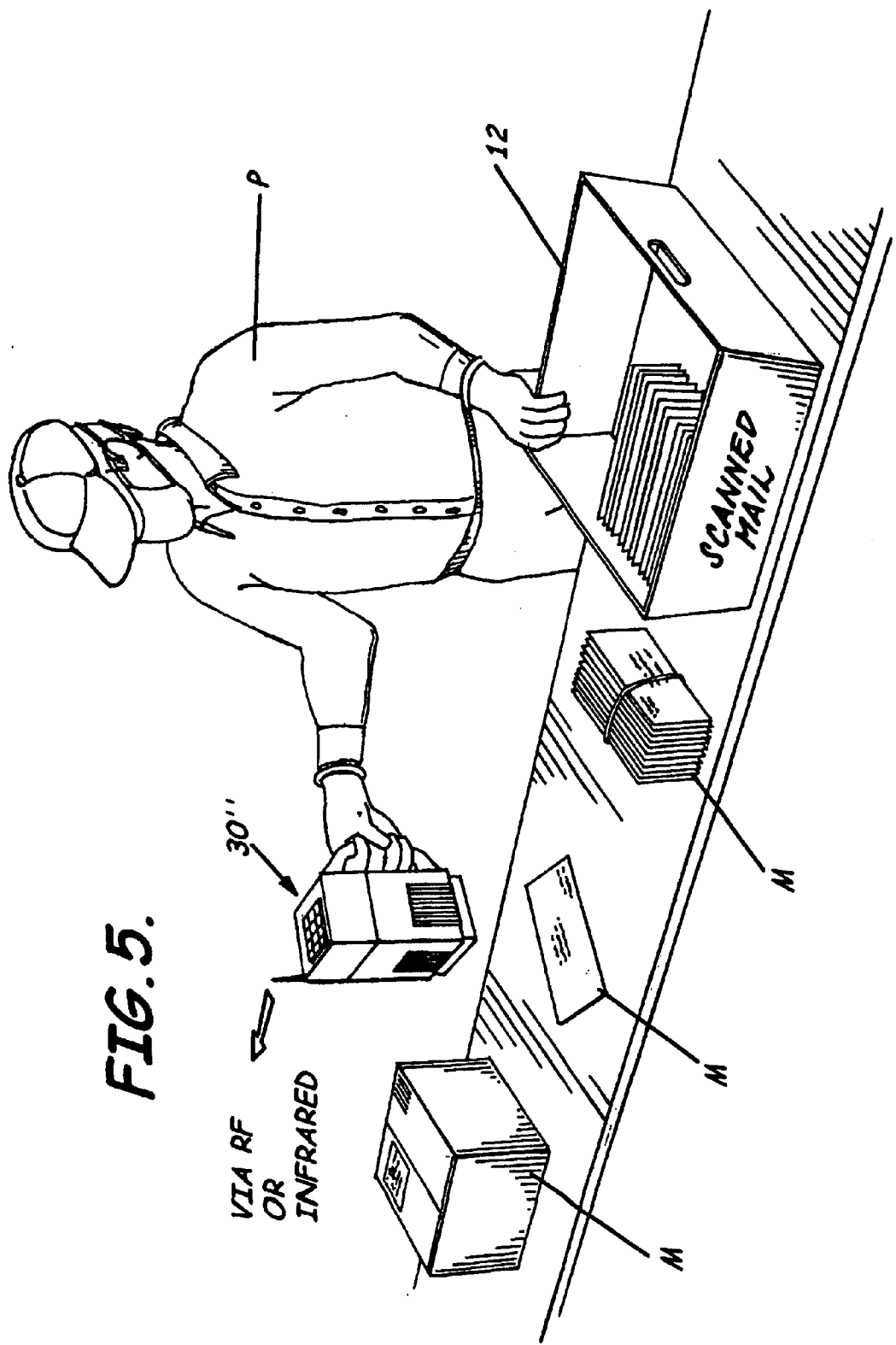
FIG. 5 is an environmental perspective view of a system for detecting harmful agents in contents of mail according to a first embodiment of the present invention.
Figure 6:
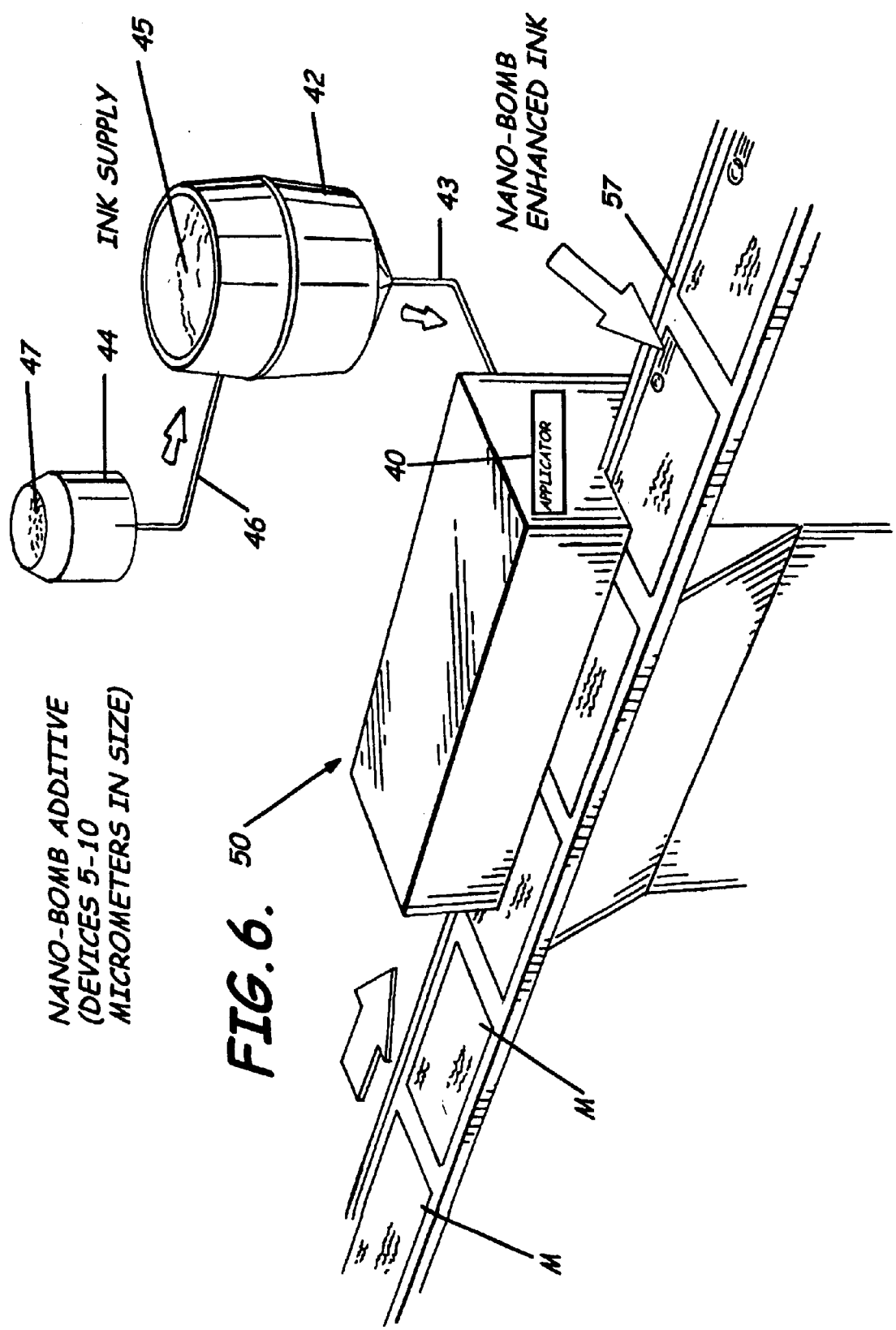
FIG. 6 is an environmental perspective view of a system for detecting harmful agents in contents of mail which disables harmful agents in contents when detected, when not detected, or when all mail passes through regardless of a detection status according to a second embodiment of the present invention.
Figure 7:
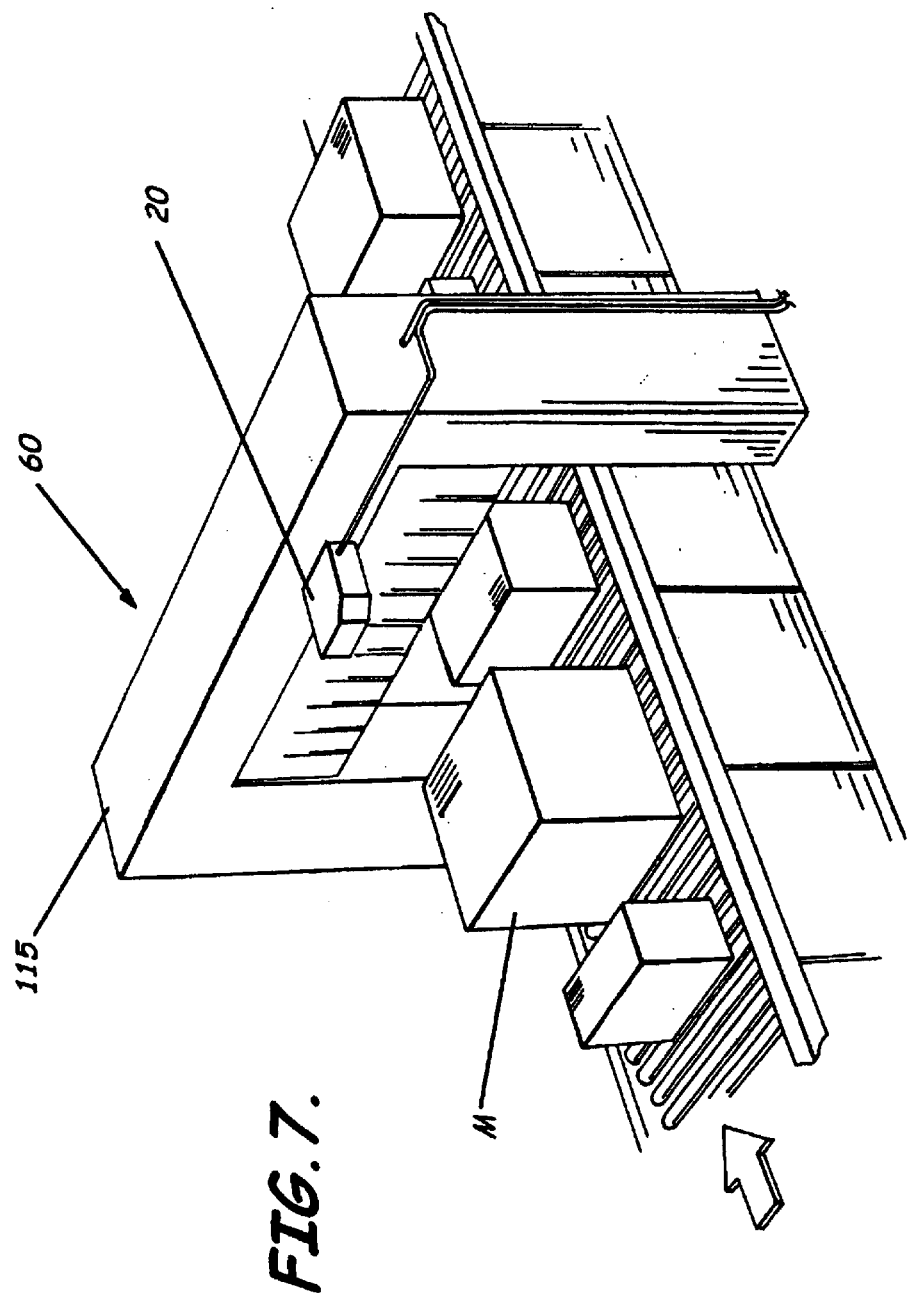
FIG. 7 is an environmental perspective view of a bar code sensor having a harmful agents sensor associated therewith of a system for detecting harmful agents in contents of mail which detects contents of parcels according to a first embodiment of the present invention.
Figure 8:
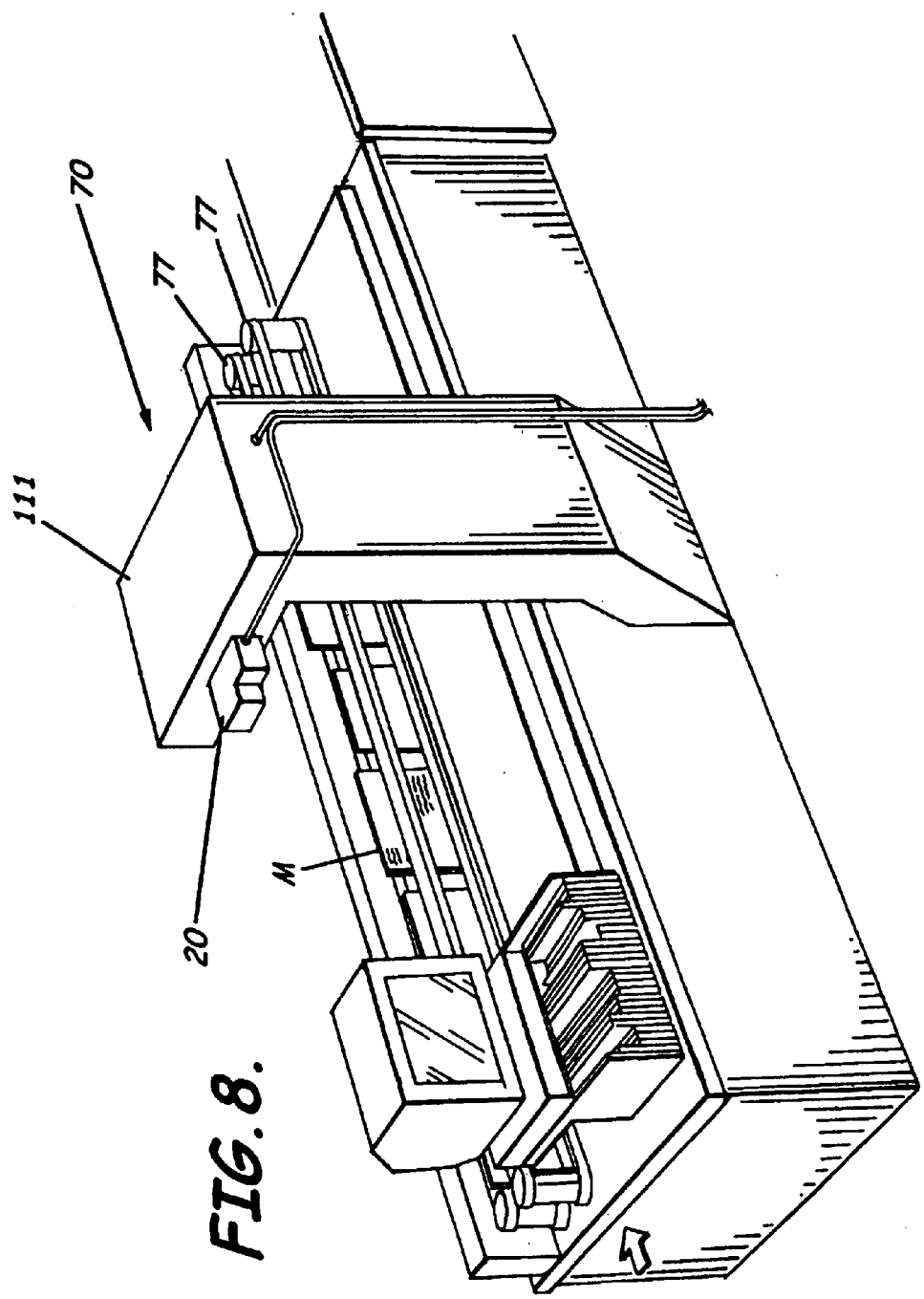
FIG. 8 is an environmental perspective view of an optical character reader having a harmful agents sensor associated therewith of a system for detecting harmful agents in contents of mail which detects flats according to a first embodiment of the present invention.
Figure 9:
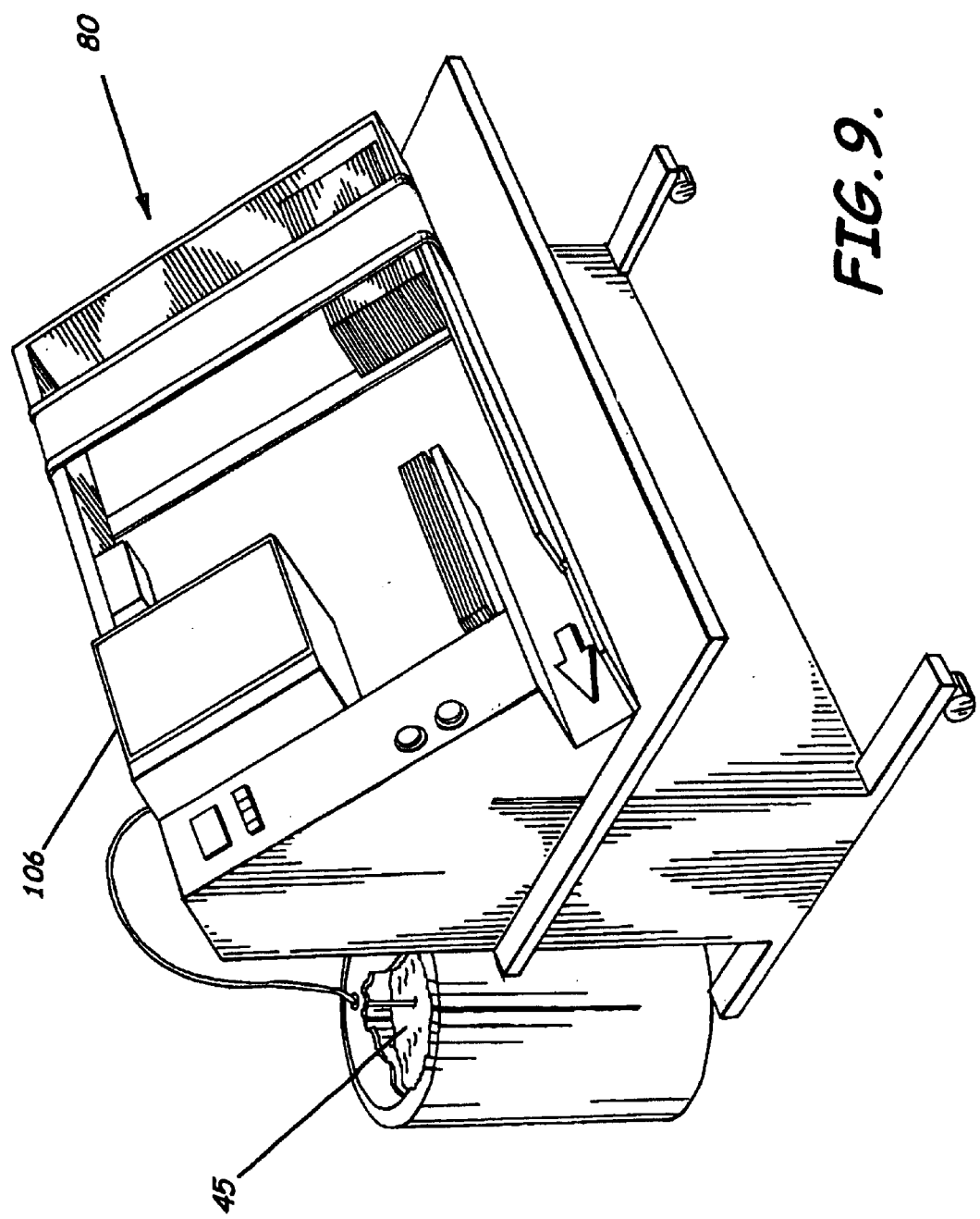
FIG. 9 is an environmental perspective view of a canceler having ink associated therewith and a harmful agents sensor positioned upstream from the canceler of a system for detecting harmful agents in contents of mail which detects letters according to a first embodiment of the present invention.

As also shown in FIGS. 1 and 4, the preferred method of detection for flats is similar to that of letters except the equipment is typically called a Model 15 flats canceler 111. This equipment also separates and mechanically cancels that mailpiece, although at a substantially slower speed than letters. An automated sorter 112 can then receive the mail, redundantly sense if desired, and then reject to a manual case or pass the mail M on to a delivery unit or other destination 118. Because the canceler 111 physically touches the envelope and causes the contents to be "shifted and shaken-up"

it advantageously allows certain biological, germ, or chemical sensors 20 to examine each mailpiece M as they pass by the device therefore detecting these harmful agents inside or associated with the mail M.

Alternatively, or in addition to the above, the present invention also provides a system 15' of detecting and disabling harmful agents in mail M which applies a "nanobomb" or other disabling agent in mail processing fluid such as associated with ink 45 in a mail canceling station 106 where ink 45 is often applied. For example, within the ink pad, ink material itself, or other locations within a piece of equipment 106, 107, 108, 109, 111, 112, 115, a disabling biological or chemical agent or reactant can be located so that when individual pieces of mail M are stamped, marked, or written on as being canceled, marked, or processed, the postal workers or personnel P handling mail M have increased confidence that mail M passing through the station is disabled or decontaminated. So, in essence, detection or mass processing is provided by the disabling agent itself within the ink 45 or other locations to which the ink 45 is associated, e.g., applied to material of the pad itself of an ink pad. Also, such nanobomb material 47 could be located within or associated with adhesive material such as labels, tabs, stamps, or the containers themselves, e.g., envelopes, cartons, boxes, or filler material.

A method of detection for parcels is to ensure separation is performed by mechanical equipment prior to directing the sensing devices towards the parcel. The equipment used for processing parcels is more varied but requires that the piece be separated prior to the sortation process. Accordingly, hand cancelling 113 and/or a small parcel and bundle sorter 115 can be used as well as understood by those skilled in the art (see FIGS. 1,4, and 6-7).

It is also realistic that different categories of mail can require different sensors 20 or levels of detection. In some cases, the detection will be from the outside of the package, and in some cases, the detection is a process of "looking through" the package using traditional contact methods or noncontact methods such as light, X-ray, radio frequency, or sound waves. Molecular electronics in various tests have shown that with the creation of "nano-bombs" which are molecular size droplets, roughly 1/5000 the size of the head of a pin which are designed to "blow-up" various microscopic enemies, including anthrax and small pox, will render the infected piece harmless.

The present invention preferably uses a sensing device or devices 20 that will detect the presence of biological, germ, chemical, or other harmful agents in the handling and processing locations of postal service companies engaged in the distribution or postal industries. This device or devices will detect the presence of these agents on or within the mailpiece when mailpieces or packages are processed on high speed equipment 106, 107, 108, 109, 111, 112, 115 currently utilized by postal or distribution companies.

These systems 15, 15' advantageously can manage the flow of mail M in such a manner that all mailpieces of unknown origin or deposited by unknown individuals will be processed on postal equipment. This equipment will separate and sense each mailpiece M with the purpose of determining if there is a dangerous or harmful agent deposited on or within the mailpiece M. For example, the system 15 preferably provides an installed sensing device or devices 20 that will detect the presence of biological, germ, chemical, or other harmful agents in mail that is processed on culling and separation equipment.

For example, as shown in FIGS. 1,4, and 6-9, a sensing device or devices 20 that will detect the presence of harmful biological, germ or chemical agents on or in mail advantageously can be positioned in association with Multi-line Optical Character Readers (MLOCR) equipment 107, Delivery Input/Output Subsystem (DIOSS) equipment otherwise known as Optical Character Reader (OCR) equipment, Delivery Bar Code System (DBCS or MPBCS) equipment 109, Carrier Sequence Bar Code Sorter (CSBCS) equipment 108, Small Parcel and Bundle Sorter equipment 115, Automated Flat Sorting (AFSM100, FSM1000, FSM881) equipment 112, and/or Advanced Facer/Canceler System (AFCS) equipment 106. The present invention also advantageously allows and provides for the creation of procedures 110, 116 to divert mail to bio-chem inspection procedures (e.g., according to new OSHA rules) for detection of harmful agents.

Also, the present invention provides a system 15 which can send a warning or indication such as a bell, light, or signal to evacuate and isolate as well as quarantine a building and automatically call 911 from the machine directly and notify a pre-recorded message once the line picks up stating the address and situation. The system 15 can also advantageously apply a counter-active reaction agent to render the infected mailpiece harmless to humans.

As shown in FIGS. 1-9 and as described herein above, the present invention also advantageously includes methods of detecting and methods of disabling harmful agents associated with pieces of mail M. A method of detecting the presence of a harmful agent associated with mail M preferably includes smell sensing the presence of one of a plurality of harmful agents possibly associated with the contents of mail M by the use of an olfactory device 30 and indicating an alarm condition responsive to the sensed presence of one of a plurality of harmful agents. The olfactory device 30 preferably includes a memory 32 having indications of a plurality of smell sensed conditions stored therein. Each of the plurality of smell sensed conditions are preferably indicative of, associated with, or representative of at least one of a plurality of harmful agents. The smell sensing step preferably includes comparing a sensed smell with at least one of the plurality of smell sensed conditions.

The present invention also includes a method of disabling a harmful agent associated with a piece of mail M. The method preferably includes applying a harmful agent disabling fluid, e.g., liquid, gas, mist, or spray, associated with processing mail M to one or more mail pieces, e.g., to each of or a bundle, group, set, or container of a plurality of mail pieces. The fluid, for example, can advantageously include an ink material and a nanobomb material associated with the ink material. The applying step can then advantageously include applying the ink material having the nanobomb material associated therewith to each of the plurality of mail pieces such as in a cancellation, bar code, marking, or other ink application step associated with processing or handling mail.

The present invention further also includes a method of detecting harmful agents associated with a piece of mail M. The method preferably includes positioning at least one harmful agent sensor 20 to be associated with each of a plurality of pieces of mail processing equipment positioned to process a plurality of pieces of mail M, sensing the presence of a harmful agent associated with at least one of the plurality of pieces of mail M, and indicating an alarm condition responsive to the sensed presence of a harmful agent in at least one of the plurality of pieces of mail M. The step of sensing can advantageously include the use of at least one harmful agent sensor 20 as described above. The at least one harmful agent sensor preferably includes at least one of the following: an olfactory device 30, an ultraviolet device, an infrared device, an x-ray device, a laser device, a radio frequency, device, and a heat sensing device.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That claimed is:

1. A system for detecting harmful agents within the contents of mail, the system comprising:
   a plurality of pieces of mail processing equipment positioned within a mail processing facility, at least one of the plurality of pieces of mail processing equipment also being positioned to individually separate and contact a plurality of pieces of mail as the plurality of pieces of mail pass through the at least one of the plurality of pieces of mail processing equipment at a relatively high rate of speed;
   at least one harmful agent sensor positioned adjacent the at least one of the plurality of pieces of mail processing equipment to sense the presence of a harmful agent in the plurality of pieces of mail as the plurality of pieces of mail are processed by the at least one of the plurality of pieces of mail processing equipment, the at least one harmful agent sensor comprising an olfactory device positioned to sense the presence of a harmful agent within the mail;
   at least one system processor in communication with the olfactory device to process data received from the olfactory device; and
   at least one alarm indicator responsive to the at least one system processor to indicate that the olfactory device has sensed the presence of a harmful agent.

2. A system as defined in claim 1, wherein the olfactory device includes a smell sensor positioned to sense smell associated with a piece of mail, an olfactory device processor in communication with the smell sensor to process data received from the smell sensor, and memory in communication with the olfactory device processor to store smell sensing data to be processed by the olfactory device processor, and wherein the smell sensing data includes data indicating a plurality of different harmful agent smells, the plurality of different harmful agent smells comprising at least about 40 different harmful agent smells.

3. A system for detecting harmful agents within the contents of mail, the system comprising:
   a plurality of pieces of mail processing equipment positioned within a mail processing facility;
   a plurality of harmful agent sensors each positioned adjacent one of the plurality of pieces of mail processing equipment to sense the presence of a harmful agent in mail as the mail is processed by each of the plurality of pieces of mail processing equipment, each of the plurality of harmful agent sensors comprising an olfactory device positioned to sense the presence of a harmful agent within the mail to thereby define a plurality of olfactory devices;
   at least one system processor in communication with each of the plurality of olfactory devices to process data received from the plurality of olfactory devices;
   at least one alarm indicator responsive to the at least one system processor to indicate that at least one of the plurality of olfactory devices has sensed the presence of a harmful agent; and
   a harmful agent disabling fluid applicator positioned to apply a harmful agent disabling fluid to a plurality of pieces of mail being processed to thereby disable harmful agents within the plurality of pieces of mail during one of the following conditions: when all of the plurality of mail pieces pass through at least one of the plurality of pieces of mail processing equipment, when the presence of a harmful agent is detected in a mail piece being processed, or when the absence of a harmful agent is detected in a mail piece being processed.

4. A system as defined in claim 3, wherein the harmful agent disabling fluid applicator includes a fluid storage container positioned to supply the harmful agent disabling fluid for application to each of the plurality of pieces of mail, wherein the harmful agent disabling fluid comprises either a liquid or a gas, and wherein the harmful agent disabling fluid includes a nanobomb material.

5. A system for detecting harmful agents within the contents of mail, the system comprising:
   a plurality of pieces of mail processing equipment positioned within a mail processing facility;
   a plurality of harmful agent sensors each positioned adjacent one of the plurality of pieces of mail processing equipment to sense the presence of a harmful agent in mail as the mail is processed by each of the plurality of pieces of mail processing equipment, each of the plurality of harmful agent sensors comprising an olfactory device positioned to sense the presence of a harmful agent within the mail to thereby define a plurality of olfactory devices, and wherein the plurality of olfactory devices sense individually separated pieces of mail;
   at least one system processor in communication with each of the plurality of olfactory devices to process data received from the plurality of olfactory devices;
   at least one alarm indicator responsive to the at least one system processor to indicate that at least one of the plurality of olfactory devices has sensed the presence of a harmful agent; and
   a mail piece marker to individually mark individually sensed mail pieces to indicate the marked mail piece has been sensed to thereby increase the accuracy and proper identification of whether a mail piece contains a harmful agent.

6. A system for detecting harmful agents within the contents of mail, the system comprising:
   at least one piece of mail processing equipment positioned within a mail processing facility to individually separate and contact a plurality of pieces of mail as the plurality of pieces of mail pass through the at least one piece of mail processing equipment at a relatively high rate of speed;
   at least one harmful agent sensor positioned adjacent the at least one piece of mail processing equipment to sense the presence of a harmful agent in each individual piece of mail as the mail is processed by the at least one piece of mail processing equipment, the at least one harmful agent sensor comprising an olfactory device;
   at least one system processor in communication with the olfactory device to process data received therefrom; and
   at least one alarm indicator responsive to the at least one system processor to indicate that the olfactory device has sensed the presence of a harmful agent.

7. A system as defined in claim 6, wherein the olfactory device includes a smell sensor positioned to sense smell associated with a piece of mail, an olfactory device processor in communication with the smell sensor to process data received from the smell sensor, and memory in communication with the olfactory device processor to store smell sensing data to be processed by the olfactory device processor, and wherein the smell sensing data includes data indicating a plurality of different harmful agent smells, the plurality of different harmful agent smells comprising at least about 40 different harmful agent smells.

8. A system for detecting harmful agents within the contents of mail, the system comprising:
   at least one piece of mail processing equipment positioned within a mail processing facility;
   at least one harmful agent sensor positioned adjacent the at least one piece of mail processing equipment to sense the presence of a harmful agent in each individual piece of mail as the mail is processed by the at least one piece of mail processing equipment, the at least one harmful agent sensor comprising an olfactory device;
   at least one system processor in communication with the olfactory device to process data received therefrom;
   at least one alarm indicator responsive to the at least one system processor to indicate that the olfactory device has sensed the presence of a harmful agent; and
   a harmful agent disabling fluid applicator positioned to apply a harmful agent disabling fluid to a plurality of pieces of mail being processed to thereby disable harmful agents within the plurality of pieces of mail during one of the following conditions: when all of the plurality of mail pieces pass through the at least one piece of mail processing equipment, when the presence of a harmful agent is detected in a mail piece being processed, or when the absence of a harmful agent is detected in a mail piece being processed.

9. A system as defined in claim 8, wherein the harmful agent disabling fluid applicator includes a fluid storage container positioned to supply the harmful agent disabling fluid for application to one or more of the plurality of pieces of mail.

10. A system for detecting harmful agents within the contents of mail, the system comprising:
   at least one piece of mail processing equipment positioned within a mail processing facility;
   at least one harmful agent sensor positioned adjacent the at least one piece of mail processing equipment to sense the presence of a harmful agent in each individual piece of mail as the mail is processed by the at least one piece of mail processing equipment, the at least one harmful agent sensor comprising an olfactory device, wherein the olfactory device senses individually separated pieces of mail;
   at least one system processor in communication with the olfactory device to process data received therefrom;
   at least one alarm indicator responsive to the at least one system processor to indicate that the olfactory device has sensed the presence of a harmful agent; and
   a mail piece marker to individually mark individually sensed mail pieces to indicate the marked mail piece has been sensed to thereby increase the accuracy and proper identification of whether a mail piece contains a harmful agent.

11. A method of detecting the presence of a harmful agent associated with mail, the method comprising:
   smell sensing the presence of at least one of a plurality of harmful agents possibly associated with the contents of mail by the use of an olfactory device, the olfactory device including a memory having indications of a plurality of smell sensed conditions stored therein, each of the plurality of smell sensed conditions being indicative of at least one of a plurality of harmful agents;
   indicating an alarm condition responsive to the sensed presence of one of the plurality of harmful agents; and
   individually marking sensed pieces of mail to indicate a marked mail piece has been sensed to thereby increase the accuracy and proper identification of whether a mail piece contains a harmful agent.

12. A method as defined in claim 11, wherein the smell sensing step includes comparing a sensed smell with at least one of the plurality of smell sensed conditions, the method further comprises storing a plurality of harmful agent smells within the memory, and wherein the plurality of harmful agent smells comprises at least about 40 different harmful agent smells.

13. A method of detecting the presence of a harmful agent associated with mail, the method comprising:
   smell sensing the presence of at least one of a plurality of harmful agents possibly associated with the contents of mail by the use of an olfactory device, the olfactory device including memory having indications of a plurality of smell sensed conditions stored therein, each of the plurality of smell sensed condition being indicative of at least one of the plurality of harmful agents;
   individually separating pieces of mail prior to the step of sensing, wherein the step of sensing includes sensing the individually separated pieces of mail;
   indicating an alarm condition responsive to the sensed presence of one of the plurality of harmful agents; and
   individually marking sensed pieces of mail to indicate a marked mail piece has been sensed to thereby increase the accuracy and proper identification of whether a mail piece contains a harmful agent.

14. A method of detecting harmful agents associated with a piece of mail, the method comprising:
   positioning at least one harmful agent sensor to be associated with each of a plurality of pieces of mail processing equipment positioned to process a plurality of pieces of mail and to individually separate and contact the plurality of pieces of mail as the plurality of pieces of mail pass through each of the plurality of pieces of mail processing equipment at a relatively high rate of speed;
   sensing the presence of a harmful agent associated with at least one of the plurality of pieces of mail; and
   indicating an alarm condition responsive to the sensed presence of a harmful agent in at least one of the plurality of pieces of mail.

15. A method as defined in claim 14, wherein the step of sensing includes the use of at least one harmful agent sensor, the at least one harmful agent sensor including one or more of the following: an olfactory device, an ultraviolet device, an infrared device, an x-ray device, a laser device, and a heat sensing device.

16. A method of detecting harmful agents associated with a piece of mail, the method comprising:
   positioning at least one harmful agent sensor to be associated with each of a plurality of pieces of mail processing equipment positioned to process a plurality of pieces of mail;
   sensing the presence of a harmful agent associated with at least one of the plurality of pieces of mail;
   individually separating the plurality of pieces of mail prior to the step of sensing, and wherein the step of sensing includes sensing the individually separated pieces of mail;
   indicating an alarm condition responsive to the sensed presence of a harmful agent in at least one of the plurality of pieces of mail; and
   individually marking sensed pieces of mail to indicate a marked mail piece has been sensed to thereby increase the accuracy and proper identification of whether a mail piece contains a harmful agent.

17. A method as defined in claim 11, further comprising the step of contactingly capturing each of a plurality of separate pieces of mail between a plurality of belts as the plurality of separate pieces of mail travel at a relatively high rate of speed prior to the step of smell sensing.

18. A method as defined in claim 14, wherein the positioning step includes contactingly capturing each of a plurality of separate pieces of mail between a plurality of belts as the plurality of separate pieces of mail travel at a relatively high rate of speed prior to the step of smell sensing.

19. A system for detecting harmful agents within the contents of mail, the system comprising:

at least one piece of mail processing equipment adapted to be positioned within a mail processing facility to individually separate and contactingly capture each of a plurality of pieces of mail between a plurality of belts as the plurality of pieces of mail pass through the at least one piece of mail processing equipment at a relatively high rate of speed;

at least one harmful agent sensor adapted to be positioned adjacent the at least one piece of mail processing equipment to sense the presence of a harmful agent in each individual piece of mail as the mail is processed by the at least one piece of mail processing equipment;

at least one system processor in communication with the at least one harmful agent sensor to process data received therefrom; and at least one alarm indicator responsive to the at least one system processor to indicate that the at least one harmful agent sensor has sensed the presence of a harmful agent.

20. A method of detecting the presence of a harmful agent associated with mail, the method comprising the steps of:

contactingly capturing each of a plurality of separate pieces of mail between a plurality of belts as the plurality of separate pieces of mail travel at a relatively high rate of speed;

sensing the presence of one of a plurality of harmful agents possibly associated with the contents of mail by the use of a harmful agent sensor after the mail has been contactingly captured between a plurality of belts; and indicating an alarm condition responsive to the sensed presence of one of a plurality of harmful agents.

21. A system for detecting harmful agents within the contents of mail, the system comprising:

a plurality of pieces of mail processing equipment positioned within a mail processing facility, at least one of the plurality of pieces of mail processing equipment comprising a canceller also being positioned to individually separate and contact a plurality of pieces of mail as the plurality of pieces of mail pass through the canceller at a relatively high rate of speed;

a harmful agent sensor positioned adjacent the canceller to sense the presence of a harmful agent in the plurality of pieces of mail as the plurality of pieces of mail are processed by the canceller, the harmful agent sensor comprising an olfactory device positioned to sense the presence of a harmful agent within the mail;

a system processor in communication with the olfactory device to process data received from the olfactory device; and an alarm indicator responsive to the system processor to indicate that the olfactory device has sensed the presence of a harmful agent.

22. A system for detecting harmful agents within the contents of mail, the system comprising:

a piece of mail processing equipment comprising a canceller positioned within a mail processing facility;

a harmful agent sensor positioned adjacent the canceller to sense the presence of a harmful agent in each individual piece of mail as the mail is processed by the canceller, the harmful agent sensor comprising an olfactory device; a system processor in communication with the olfactory device to process data received therefrom;

an alarm indicator responsive to the system processor to indicate that the olfactory device has sensed the presence of a harmful agent; and a harmful agent disabling fluid applicator positioned to apply a harmful agent disabling fluid to a plurality of pieces of mail being processed to thereby disable harmful agents within the plurality of pieces of mail during one of the following conditions: when all of the plurality of mail pieces pass through the canceller, when the presence of a harmful agent is detected in a mail piece being processed, or when the absence of a harmful agent is detected in a mail piece being processed.

23. A system for detecting harmful agents within the contents of mail, the system comprising:

a piece of mail processing equipment comprising a canceller positioned within a mail processing facility;

a harmful agent sensor positioned adjacent the canceller to sense the presence of a harmful agent in each individual piece of mail as the mail is processed by the canceller, the harmful agent sensor comprising an olfactory device, wherein the olfactory device senses individually separated pieces of mail;

a system processor in communication with the olfactory device to process data received therefrom;

an alarm indicator responsive to the system processor to indicate that the olfactory device has sensed the presence of a harmful agent; and a mail piece marker to individually mark individually sensed mail pieces to indicate the marked mail piece has been sensed to thereby increase the accuracy and proper identification of whether a mail piece contains a harmful agent.

24. A system for detecting harmful agents within the contents of mail, the system comprising:

a piece of mail processing equipment comprising a canceller positioned within a mail processing facility to individually separate and contactingly capture each of a plurality of pieces of mail between a plurality of belts as the plurality of pieces of mail travel through the canceller at a relatively high rate of speed, the plurality of pieces of mail including a large quantity of either a plurality of letters of a plurality of flats;

a harmful agent sensor comprising an olfactory device positioned adjacent the canceller to sense the presence of a harmful agent in each individually separated piece of mail as the plurality of pieces of mail are processed by the canceller, the canceller contacting each of the plurality of pieces of mail to disrupt the contents of each of the plurality of pieces of mail to thereby enhance detection of the presence of harmful agents by the olfactory device;

a system processor in communication with the olfactory device to process data received therefrom; and an alarm indicator responsive to the system processor to indicate that the olfactory device has sensed the presence of a harmful agent.

* * * * *